United States Patent [19]

Van Allan et al.

[11] 4,146,707

[45] Mar. 27, 1979

[54] HETEROCYCLIC ETHENYL OR VINYL HETEROCYCLIC OR AROMATIC COMPOUNDS FOR MIGRATION IMAGING PROCESSES

[75] Inventors: James A. Van Allan; Frank G. Webster; George A. Reynolds, all of Rochester, N.Y.

[73] Assignee: Eastman Kodak Company, Rochester, N.Y.

[21] Appl. No.: 874,078

[22] Filed: Feb. 1, 1978

Related U.S. Application Data

[62] Division of Ser. No. 816,128, Jul. 15, 1977.

[51] Int. Cl.$^2$ .................. C07D 309/28; C07D 407/14; C07D 405/06; C07D 409/14

[52] U.S. Cl. .................................... 542/433; 542/445; 542/447; 542/449; 542/434; 542/448; 260/329 F; 260/329 HS; 260/345.1

[58] Field of Search ............... 542/447, 433, 445, 465, 542/448

[56] References Cited

U.S. PATENT DOCUMENTS 4,012,376 3/1977 Wright ................................ 542/447

FOREIGN PATENT DOCUMENTS 2617345 11/1976 Fed. Rep. of Germany ........... 542/448

*Primary Examiner*—Allen B. Curtis

*Attorney, Agent, or Firm*—John R. Everett

[57] ABSTRACT

Novel compounds having the following structure

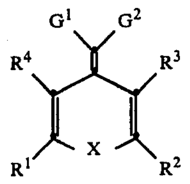

wherein

X represents O, S or NR and R is benzyl or butyl;

$G^1$ and $G^2$ represent cyano or taken together with the carbon atom to which they are attached represent sufficient atoms to complete an ethyl substituted barbituric acid nucleus;

$R^1$ and $R^2$, which may be the same or different represent phenyl, $(-CH=)_nA^1$, $-CH=CH-A^2$; and $R^3$, $R^4$, $A^1$, $A^2$ and n are as stated in the detailed disclosure.

8 Claims, 1 Drawing Figure

HETEROCYCLIC ETHENYL OR VINYL HETEROCYCLIC OR AROMATIC COMPOUNDS FOR MIGRATION IMAGING PROCESSES

This is a divisional of U.S. patent application Ser. No. 816,128 filed by Van Allan et al. on July 15, 1977.

FIELD OF THE INVENTION

This invention relates to electrophoretic migration imaging processes and, in particular, to the use of certain photosensitive pigment materials in such processes.

BACKGROUND OF THE INVENTION

In the past, there has been extensive description in the patent and other technical literature of electrophoretic migration imaging processes. For example, a description of such processes may be found in U.S. Pat. Nos. 2,758,939 by Sugarman issued Aug. 14, 1956; 2,940,847, 3,100,426, 3,140,175 and 3,143,508, all by Kaprelian; 3,384,565, 3,384,488 and 3,615,558, all by Tulagin et al; 3,384,566 by Clark; and 3,383,993 by Yeh. In addition to the foregoing patent literature directed to conventional photoelectrophoretic migration imaging processes, another type of electrophoretic migration imaging process which advantageously provides for image reversal is described in Groner, U.S. Pat. No. 3,976,485 issued Aug. 24, 1976. This latter process has been termed photoimmobilized electrophoretic recording or PIER.

In general, each of the foregoing electrophoretic migration imaging processes typically employs a layer of electrostatic charge-bearing photoconductive particles, i.e., electrically photosensitive particles, positioned between two spaced electrodes, one of which may be transparent. To achieve image formation in these processes, the charge-bearing photosensitive particles positioned between the two spaced electrodes, as described above, are subjected to the influence of an electric field and exposed to activating radiation. As a result, the charge-bearing electrically photosensitive particles are caused to migrate electrophoretically to the surface of one or the other of the spaced electrodes, and one obtains an image pattern on the surface of these electrodes. Typically, a negative image is formed on one electrode, and a positive image is formed on the opposite electrode. Image discrimination occurs in the various electrophoretic migration imaging processes as a result of a net change in charge polarity of either the exposed electrically photosensitive particles (in the case of conventional electrophoretic migration imaging) or the unexposed electrically photosensitive particles (in the case of the electrophoretic migration imaging process described in the above-noted Groner patent) so that the image formed on one electrode surface is composed ideally of electrically photosensitive particles of one charge polarity, either negative or positive polarity, and the image formed on the opposite polarity electrode surface is composed ideally of electrically photosensitive particles having the opposite charge polarity, either positive or negative respectively.

In any case, regardless of the particular electrophoretic migration imaging process employed, it is apparent that an essential component of any such process is the electrically photosensitive particles. And, of course, to obtain an easy-to-read, visible image it is important that these electrically photosensitive particles be colored, as well as electrically photosensitive. Accordingly, there exists a continuing effort to find particles which possess both useful levels of electrical photosensitivity and which exhibit good colorant properties. Thus, various types of electrically photosensitive materials are disclosed for use in electrophoretic migration imaging processes. See for example U.S. Pat. Nos. 2,758,939 by Sugarman, 2,940,847 by Kaprelian, and 3,384,488 and 3,615,558 by Tulagin et al., noted hereinabove.

Useful electrically photosensitive or photoconductive pigment materials for electrophoretic migration imaging usually have been frequently selected from known classes of photoconductive materials which may be employed in conventional photoconductive elements, e.g., photoconductive plates, drums, or webs used in electrophotographic office-copier devices. For example, both Sugarman and Kaprelian in the above-referenced patents state that electrically photosensitive materials useful in electrophoretic migration imaging processes may be selected from known classes of photoconductive materials. Also, the phthalocyanine pigments described as a useful electrically photosensitive material for electrophoretic imaging processes in U.S. Pat. No. 3,615,558 by Tulagin et al. have long been known to exhibit useful photoconductive properties.

SUMMARY OF THE INVENTION

In accord with the present invention, a group of novel compounds have been discovered which are useful in electrophoretic migration imaging processes. To the best of our knowledge, none of said materials have been previously identified as photoconductors. Said compounds have the following structure:

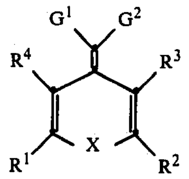

I.

wherein

X represents O, S or NR and R is benzyl or butyl;

$G^1$ and $G^2$ represent cyano or taken together with the carbon atom to which they are attached represent sufficient atoms to complete an ethyl substituted barbituric acid nucleus;

$R^1$ and $R^2$, which may be the same or different represent phenyl, $(-CH=)_nA^1$, $-CH=CH-A^2$;

$R^3$ and $R^4$ represent hydrogen or $R^3$ together with $R^2$ or $R^4$ together with $R^1$ represent sufficient atoms to form a fused substituted six membered saturated carbocyclic ring and said carbocyclic ring substituents are selected from the group consisting of 2,3,6,7-tetrahydro-1H,5H-benzo[ij]quinolizin-9-ylmethylene and 4-(N,N-dimethylamino)benzylidene;

$A^1$ represents 3-ethylbenzoxazolin-2-ylidene or 2,6-diphenyl-4H-pyran-4-ylidene;

$A^2$ represents anthracene-9-yl; 2,3,6,7-tetrahydro-1H,5H-benzo[ij]quinolizin-9-yl; 2-styrylthien-5-yl; 1,2,3,4-tetrahydro-1-methylquinolin-6-yl; 4-(N,N-dimethylamino)phenyl and 4-(N,N-diethylamino)-2-methoxyphenyl; and n represents 1 or 3.

Charge-bearing, electrically photosensitive particles formulated from the compounds of the present invention are positioned between two spaced electrodes. Preferably these particles are contained in an electrically insulating carrier such as an electrically insulating liquid or an electrically insulating, liquefiable matrix material, e.g., a thixotropic or a heat- and/or solvent-softenable material, which is positioned between the spaced electrodes. While so positioned between the spaced electrodes, the photosensitive particles are subjected to an electric field and exposed to a pattern of activating radiation. As a consequence, the charge-bearing, electrically photosensitive particles undergo a radiation-induced variation in their charge polarity and migrate to one or the other of the electrode surfaces to form on at least one of these electrodes an image pattern representing a positive-sense or negative-sense image of the original radiation exposure pattern.

DESCRIPTION OF THE PREFERRED EMBODIMENTS

Figure 1:
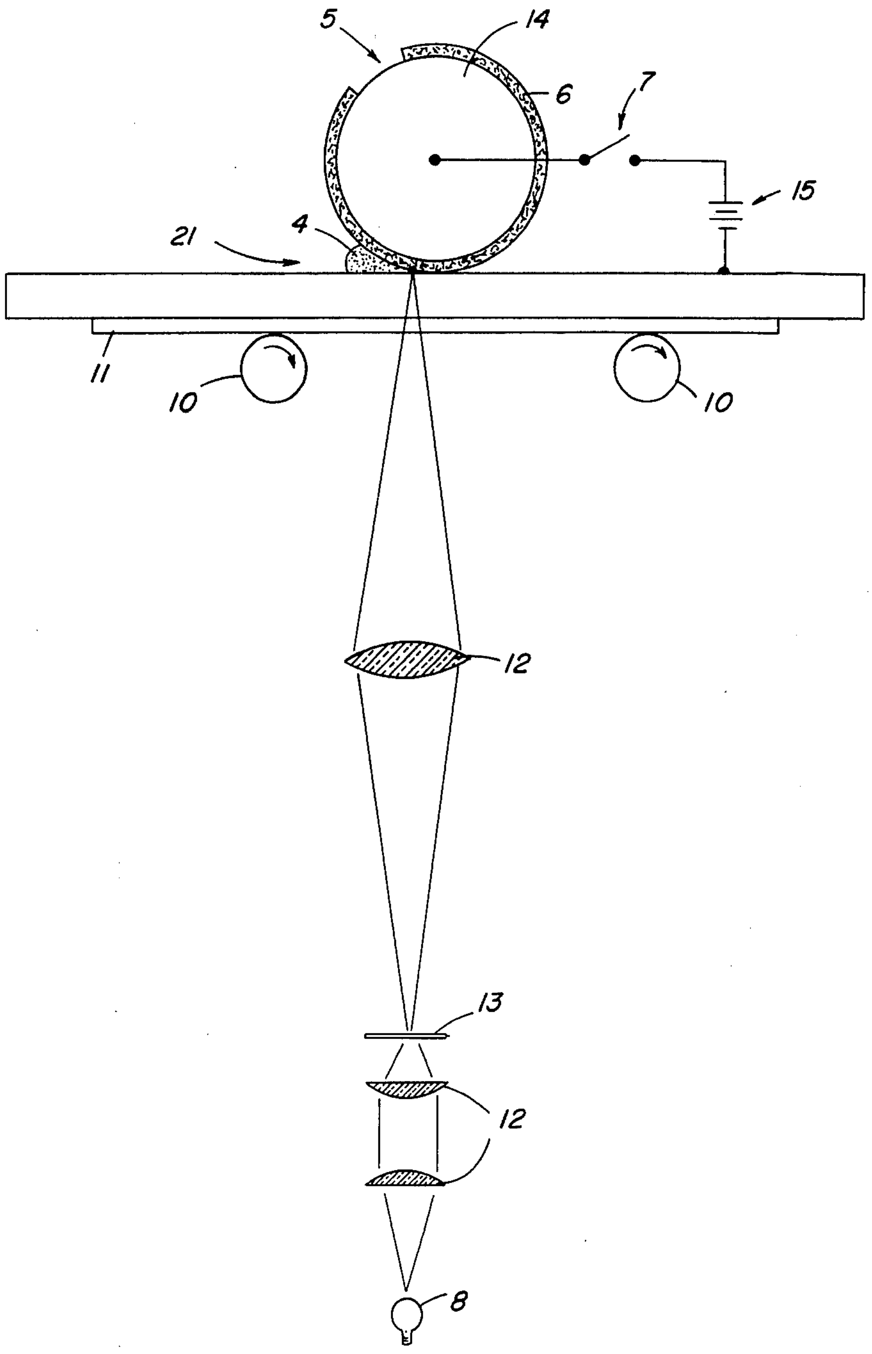
FIG. 1 represents diagrammatically a typical imaging apparatus for carrying out a photoelectrophoretic migration imaging process using the compounds of the invention.

In accordance with one embodiment the present invention there is provided a group of compounds which are useful in photoelectrophoretic migration imaging processes. Said materials have a structure according to general Formula I wherein:

X represents 0;

$G^1$ and $G^2$ represent cyano;

$R^1$ and $R^2$ are the same and represent —CH=•CH—$A^2$;

$A^2$ represent anthracene-9-yl or 2,3,6,7-tetrahydro-1H,5H-benzo[ij]quinolizin-9-yl and 2-styrylthien-5-yl; and $R^3$ and $R^4$ represent hydrogen.

In accordance with another embodiment of the present invention there are provided compounds according to general Formula I wherein:

X represents O;

$G^1$ and $G^2$ represent cyano;

$R^1$ represents —CH=$A^1$ and $A^1$ represents 2,6-diphenyl-4H-pyran-4-ylidene;

$R^2$ represents —CH=CH—$A^2$ and $A^2$ represents anthracen-9-yl or 2,3,6,7-tetrahydro-1H,5H-benzo[ij]quinolizin-9-yl; and $R^3$ and $R^4$ represent hydrogen.

In accordance with another embodiment of the present invention, there are provided compounds according to general Formula I wherein X represents S;

$G^1$ and $G^2$ represent cyano;

$R^1$ and $R^2$ are the same and represent —CH=•CH—$A^2$;

$A^2$ represents 2,3,6,7-tetrahydro-1H,5H-benzo[ij]quinolizin-9-yl or 1,2,3,4-tetrahydro-N-methylquinolin-6-yl; and $R^3$ and $R^4$ are hydrogen.

In accordance with yet another embodiment of the present invention there are provided compounds according to general Formula I wherein X represents NR and R is butyl or benzyl;

$G^1$ and $G^2$ represent cyano;

$R^1$ and $R^2$ are the same and represent —CH=•CH—$A^2$;

$A^2$ represents 4-(N,N-dimethylamino)phenyl, 2,3,6,7-tetrahydro-1H,5H-benzo[ij]quinolizin-9-yl or 4-(N,N-diethylamino)-2-methoxyphenyl; and $R^3$ and $R^4$ represent hydrogen.

In accordance with yet another embodiment of the present invention there are provided compounds according to general Formula I wherein X represents 0;

$G^1$ and $G^2$ are each cyano or together with the carbon atom to which they are attached represent sufficient atoms to form an ethyl substituted barbituric acid nucleus;

$R^1$ represents phenyl;

$R^2$ represents —CH=CH—CH=$A^1$ or —CH=•CH—$A^2$;

$A^1$ represents 3-ethylbenzoxazolin-2-ylidene;

$A^2$ represents 2,3,6,7-tetrahydro-1H,5H-benzo[ij]quinolizin-9-yl; and $R^3$ and $R^4$ represent hydrogen.

In accordance with yet another embodiment of the present invention, there are provided compounds according to general Formula I wherein X represents O;

$G^1$ and $G^2$ represent cyano;

$R^3$ together with $R^2$ and $R^1$ together with $R^4$ represent sufficient atoms to form a fused substituted six-membered saturated carbocyclic ring; and said carbocyclic ring substituents are selected from the group consisting of 2,3,6,7-tetrahydro-1H,5H-benzo[ij]quinolizin-9-ylmethylene and 4-(N,N-dimethylamino)-benzylidene.

In general the materials of Formula I which have been found to be electrophotosensitive tend to exhibit a maximum absorption wavelength, λmax, within the range of from about 420 to about 750 nm. A variety of different materials within the class defined by Formula I have been tested and found to exhibit useful levels of electrical photosensitivity in electrophoretic migration imaging processes.

A partial listing of representative compounds are included herein in Table I.

TABLE I

| No. | | Color |
|---|---|---|
| 1 | 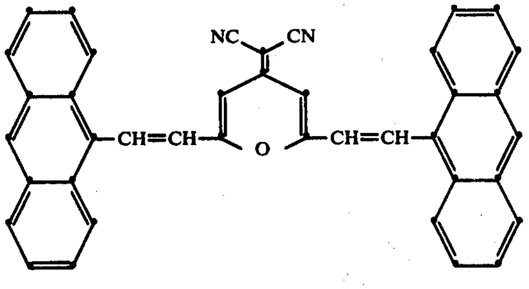 | Reddish Brown |

TABLE I-continued
| No. | | Color |
|---|---|---|
| 2 | 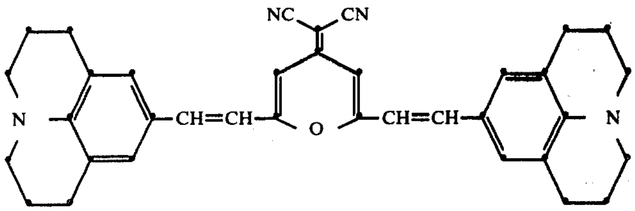 | Dark Purple |
| 3 | 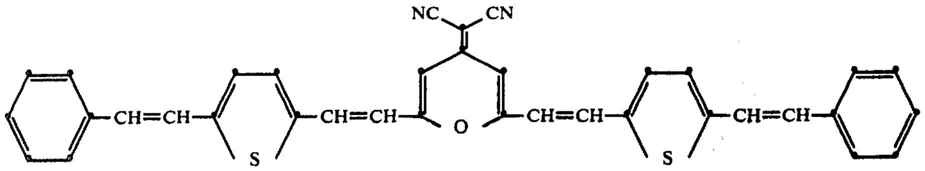 | Brown |
| 4 | 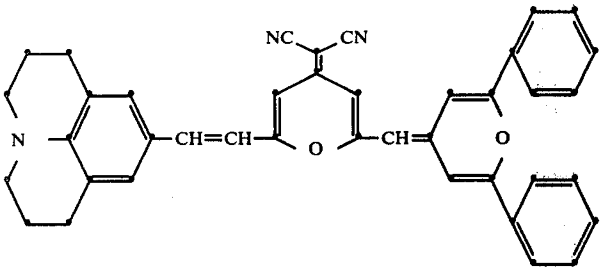 | Reddish Purple |
| 5 | 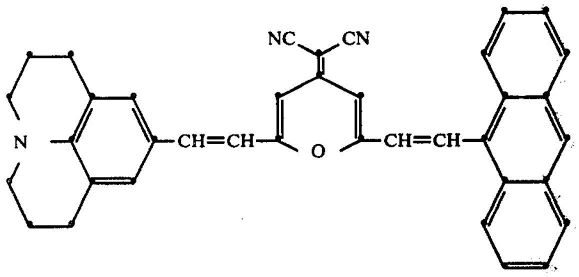 | Purple |
| 6 | 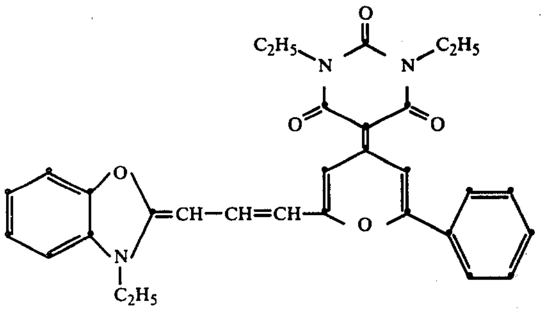 | Purple |
| 7 | 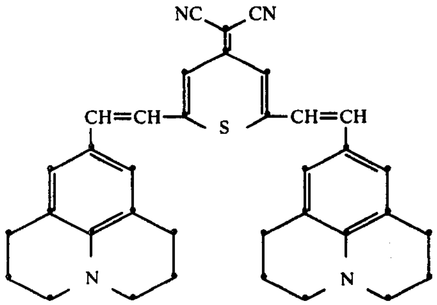 | Black |

TABLE I-continued
| No. | | Color |
|---|---|---|
| 8 | 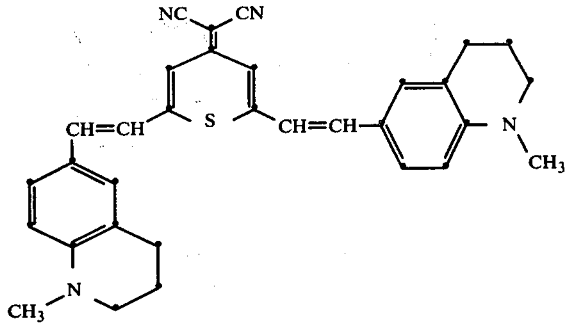 | Purplish Black |
| 9 | 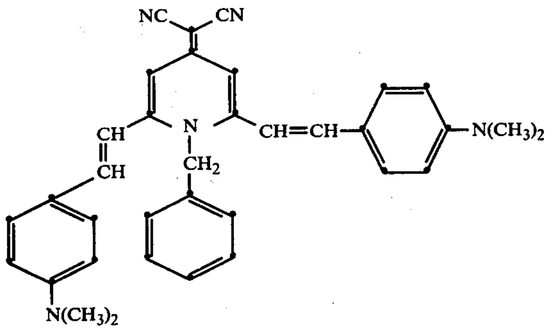 | Yellow |
| 10 | 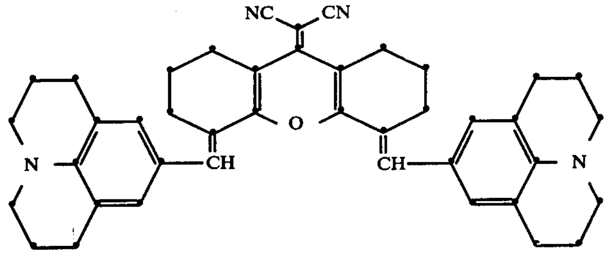 | Purple |
| 11 | 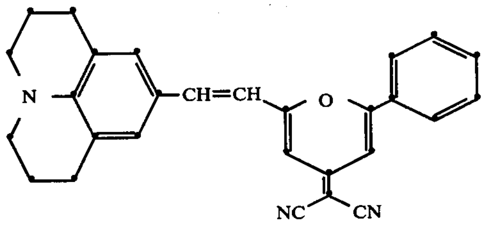 | Purplish Black |
| 12 | 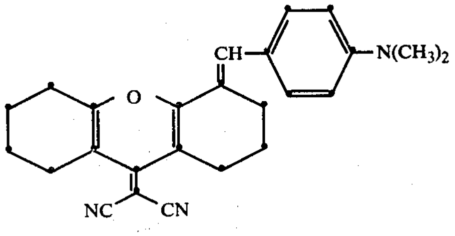 | Red |

TABLE I-continued

| No. | | Color |
|---|---|---|
| 13 | 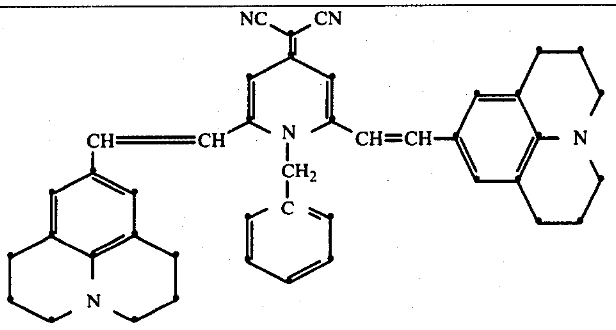 | Orange |
| 14 | 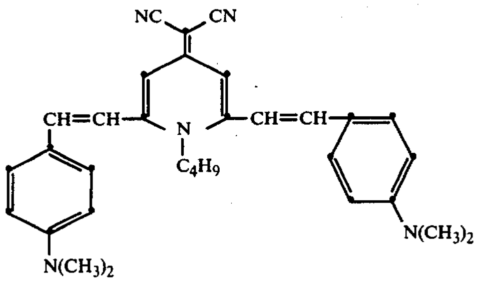 | Yellow |
| 15 | 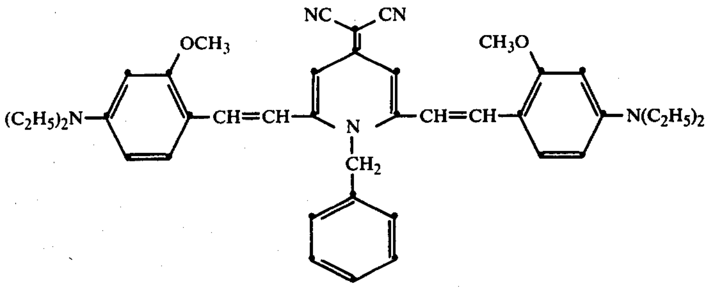 | Orange |

The materials described by general Formula I may be prepared by the various procedures. The procedures disclosed in U.S. Pat. No. 2,965,486 to Brooker et al., issued Dec. 20, 1960 may be used to prepare any of the compounds falling within the scope of general Formula I.

As indicated hereinabove, the electrically photosensitive compounds described herein are useful in the preparation of the electrically photosensitive imaging particles used in electrophoretic migration imaging processes. In general, electrically photosensitive particles useful in such processes have an average particle size within the range of from about 0.01 micron to about 20 microns, preferably from about 0.01 to about 5 microns. Typically, these particles are composed of one or more colorants such as the colorants described in the present invention. However, these electrically photosensitive particles may also contain various nonphotosensitive materials such as electrically insulating polymers, charging control agents, various organic and inorganic fillers, as well as various additional dyes or pigment materials to change or enhance various colorant and physical properties of the electrically photosensitive particle. In addition, such electrically photosensitive particles may contain other photosensitive materials such as various sensitizing dyes and/or chemical sensitizers to alter or enhance their response characteristics to activating radiation.

When used in an electrophoretic migration imaging process, the electrically photosensitive compounds described in Table I are typically positioned in particulate form, between two or more spaced electrodes, one or both of which typically are transparent to radiation to which the electrically photosensitive material is light-sensitive, i.e., activating radiation. Although the electrically photosensitive material, in particulate form, may be dispersed simply as a dry powder between two spaced electrodes and then subjected to a typical electrophoretic migration imaging operation such as that described in U.S. Pat. No. 2,758,939 by Sugarman, it is more typical to disperse the electrically photosensitive particulate material in an electrically insulating carrier, such as an electrically insulating liquid, or an electrically insulating, liquefiable matrix material, such as a heat- and/or solvent-softenable polymeric material or a thixotropic polymeric material. Typically, when one employs such a dispersion of electrically photosensitive particulate material and electrically insulating carrier material between the spaced electrodes of an electrophoretic migration imaging system, it is conventional to employ from about 0.05 part to about 2.0 parts of electrically photosensitive particulate material for each 10 parts by weight of electrically insulating carrier material.

As indicated above, when the electrically photosensitive particles used in the present invention are dispersed in an electrically insulating carrier material, such carrier material may assume a variety of physical forms and may be selected from a variety of different materials. For example, the carrier material may be a matrix of an electrically insulating, normally solid polymeric material capable of being softened or liquefied upon application of heat, solvent, and/or pressure so that the electrically photosensitive particulate material dispersed therein can migrate through the matrix. In another, more typical embodiment of the invention, the carrier material can comprise an electrically insulating liquid such as decane, paraffin, Sohio Odorless Solvent 3440 (a kerosene fraction marketed by the Standard Oil Company, Ohio), various isoparaffinic hydrocarbon liquids such as those sold under the trademark Isopar G by Exxon Corporation and having a boiling point in the range of 145° C to 186° C, various halogenated hydrocarbons such as carbon tetrachloride, trichloromonofluoromethane, and the like, various alkylated aromatic hydrocarbon liquids such as the alkylated benzenes, for example, xylenes, and other alkylated aromatic hydrocarbons such as are described in U.S. Pat. No. 2,899,335. An example of one such useful alkylated aromatic hydrocarbon liquid which is commercially available is Solvesso 100 made by Exxon Corporation. Solvesso 100 has a boiling point in the range of about 157° C to about 177° C and is composed of 9 percent dialkyl benzenes, 37 percent trialkyl benzenes, and 4 percent aliphatics. Typically, whether solid or liquid at normal room temperatures, i.e., about 22° C, the electrically insulating carrier material used in the present invention is a material having a resistivity greater than about $10^9$ ohm-cm, preferably greater than about $10^{12}$ ohm-cm. When the electrically photosensitive particles formed from the materials of the present invention are incorporated in a carrier material, such as one of the above-described electrically insulating liquids, various other addenda may also be incorporated in the resulting imaging suspension. For example, various charge control agents may be incorporated in such a suspension to improve the uniformity of charge polarity of the electrically photosensitive particles dispersed in the liquid suspension. Such charge control agents are well known in the field of liquid electrographic developer compositions where they are employed for purposes substantially similar to that described herein. Thus, extensive discussion of the materials herein is deemed unnecessary. These materials are typically polymeric materials incorporated by admixture thereof into the liquid carrier vehicle of the suspension. In addition to, and possibly related to, the aforementioned enhancement of uniform charge polarity, it has been found that the charge control agents often provide more stable suspensions, i.e., suspensions which exhibit substantially less settling out of the dispersed photosensitive particles.

In addition to the foregoing charge control agent materials, various polymeric binder materials such as various natural, semi-synthetic or synthetic resins, may be dispersed or dissolved in the electrically insulating carrier to serve as a fixing material for the final photosensitive particle image formed on one of the spaced electrodes used in electrophoretic migration imaging systems. Here again, the use of such fixing addenda is conventional and well known in the closely related art of liquid electrographic developer compositions so that extended discussion thereof is unnecessary herein.

The process of the present invention will be described in more detail with reference to the accompanying drawing, FIG. 1, which illustrates a typical apparatus which employs the electrophoretic migration imaging.

FIG. 1 shows a transparent electrode 1 supported by two rubber drive rollers 10 capable of imparting a translating motion via original image 11 to electrode 1 in the direction of the arrow. Electrode 1 may be composed of a layer of optically transparent material, such as glass or an electrically insulating, transparent polymeric support such as polyethylene terephthalate, covered with a thin, optically transparent, conductive layer such as tin oxide, indium oxide, nickel, and the like. Optionally, depending upon the particular type of electrophoretic migration imaging process desired, the surface of electrode 1 may bear a "dark charge exchange" material, such as a solid solution of an electrically insulating polymer and 2,4,7-trinitro-9-fluorenone as described by Groner in U.S. Pat. No. 3,976,485 issued Aug. 24, 1976.

Spaced opposite electrode 1 and in pressure contact therewith is a second electrode 5, an idler roller which serves as a counter electrode to electrode 1 for producing the electric field used in the electrophoretic migration imaging process. Typically, electrode 5 has on the surface thereof a thin, electrically insulating layer 6. Electrode 5 is connected to one side of the power source 15 by switch 7. The opposite side of the power source 15 is connected to electrode 1 so that as an exposure takes place, switch 7 is closed and an electric field is applied to the electrically photosensitive particulate material 4 which is positioned between electrodes 1 and 5. Typically, electrically photosensitive particulate material 4 is dispersed in an electrically insulating carrier material such as described hereinabove.

The electrically photosensitive particulate material 4 may be positioned between electrodes 1 and 5 by applying material 4 to either or both of the surfaces of electrodes 1 and 5 prior to the imaging process or by injecting electrically photosensitive imaging material 4 between electrodes 1 and 5 during the electrophoretic migration imaging process.

As shown in FIG. 1, exposure of electrically photosensitive particulate material 4 takes place by use of an exposure system consisting of light source 8, an original image 11 to be reproduced, such as a photographic transparency, a lens system 12, and any necessary or desirable radiation filters 13, such as color filters, whereby electrically photosensitive material 4 is irradiated with a pattern of activating radiation corresponding to original image 11. Although the electrophoretic migration imaging system represented in FIG. 1 shows electrode 1 to be transparent to activating radiation from light source 8, it is possible to irradiate electrically photosensitive particulate material 4 in the nip 21 between electrodes 1 and 5 without either of electrodes 1 or 5 being transparent. In such a system, although not shown in FIG. 1, the exposure source 8 and lens system 12 is arranged so that image material 4 is exposed in the nip or gap 21 between electrodes 1 and 5.

As shown in FIG. 1, electrode 5 is a roller electrode having a conductive core 14 connected to power source 15. The core is in turn covered with a layer of insulating material 6, for example, baryta paper. Insulating material 6 serves to prevent or at least substantially reduce the capability of electrically photosensitive particulate material 4 to undergo a radiation induced charge alteration upon interaction with electrode 5. Hence, the term "blocking electrode" may be used, as is conventional in the art of electrophoretic migration imaging, to refer to electrode 5.

Although electrode 5 is shown as a roller electrode and electrode 1 is shown as essentially a translatable, flat plate electrode in FIG. 1, either or both of these electrodes may assume a variety of different shapes such as a web electrode, rotating drum electrode, plate electrode, and the like as is well known in the field of electrophoretic migration imaging. In general, during a typical electrophoretic migration imaging process wherein electrically photosensitive material 4 is dispersed in an electrically insulating, liquid carrier, electrodes 1 and 5 are spaced such that they are in pressure contact or very close to one another during the electrophoretic migration imaging process, e.g., less than 50 microns apart. However, where electrically photosensitive particulate material 4 is dispersed simply in an air gap between electrodes 1 and 5 or in a carrier such as a layer of heat-softenable or other liquefiable material coated as a separate layer on electrode 1 and/or 5, these electrodes may be spaced more than 50 microns apart during the imaging process.

The strength of the electric field imposed between electrodes 1 and 5 during the electrophoretic migration imaging process may vary considerably; however, it has generally been found that optimum image density and resolution are obtained by increasing the field strength to as high a level as possible without causing electrical breakdown of the carrier medium in the electrode gap. For example, when electrically insulating liquids such as isoparaffinic hydrocarbons are used as the carrier in the imaging apparatus of FIG. 1, the applied voltage across electrodes 1 and 5 typically is within the range of from about 100 volts to about 4 kilovolts or higher.

As explained hereinabove, image formation occurs in electrophoretic migration imaging processes as the result of the combined action of activating radiation and electric field on the electrically photosensitive particulate material 4 disposed between electrodes 1 and 5 in the attached drawing. Typically, for best results, field application and exposure to activating radiation occurs concurrently. However, as would be expected, by appropriate selection of various process parameters such as field strength, activating radiation intensity, incorporation of suitable light sensitive addenda in or together with the electrically photosensitive particles formed from the material of Formula I, e.g., by incorporation of a persistent photoconductive material, and the like, it is possible to alter the timing of the exposure and field application events so that one may use sequential exposure and field application events rather than concurrent field application and exposure events.

When disposed between imaging electrodes 1 and 5 of FIG. 1, electrically photosensitive particulate material 4 exhibits an electrostatic charge polarity, either as a result of triboelectric interaction of the particles or as a result of the particles interacting with the carrier material in which they are dispersed, for example, an electrically insulating liquid, such as occurs in conventional liquid electrographic developing compositions composed of toner particles which acquire a charge upon being dispersed in an electrically insulating carrier liquid.

Image discrimination occurs in the electrophoretic migration imaging process as a result of the combined application of electric field and activating radiation on the electrically photosensitive particulate material dispersed between electrodes 1 and 5 of the apparatus shown in FIG. 1. That is, in a typical imaging operation, upon application of an electric field between electrodes 1 and 5, the particles 4 of charge-bearing, electrically photosensitive material are attracted in the dark to either electrodes 1 or 5, depending upon which of these electrodes has a polarity opposite to that of the original charge polarity acquired by the electrically photosensitive particles. And, upon exposing particles 4 to activating electromagnetic radiation, it is theorized that there occurs neutralization or reversal of the charge polarity associated with either the exposed or unexposed particles. In typical electrophoretic migration imaging systems wherein electrode 1 bears a conductive surface, the exposed, electrically photosensitive particles 4, upon coming into electrical contact with such conductive surface, undergo an alteration (usually a reversal) of their original charge polarity as a result of the combined application of electric field and activating radiation. Alternatively, in the case of photoimmobilized electrophoretic recording (PIER), wherein the surface of electrode 1 bears a dark charge exchange material as described by Groner in aforementioned U.S. Pat. No. 3,976,485, one obtains reversal of the charge polarity of the unexposed particles, while maintaining the original charge polarity of the exposed electrically photosensitive particles, as these particles come into electrical contact with the dark charge exchange surface of electrode 1. In any case, upon the application of electric field and activating radiation to electrically photosensitive particulate material 4 disposed between electrodes 1 and 5 of the apparatus shown in FIG. 1, one can effectively obtain image discrimination so that an image pattern is formed by the electrically photosensitive particles which corresponds to the original pattern of activating radiation. Typically, using the apparatus shown in FIG. 1, one obtains a visible image on the surface of electrode 1 and a complementary image pattern on the surface of electrode 5.

Subsequent to the application of the electric field and exposure to activating radiation, the images which are formed on the surface of electrodes 1 and/or 5 of the apparatus shown in FIG. 1 may be temporarily or permanently fixed to these electrodes or may be transferred to a final image receiving element. Fixing of the final particle image can be effected by various techniques, for example, by applying a resinous coating over the surface of the image bearing substrate. For example, if electrically photosensitive particles 4 are dispersed in a liquid carrier between electrodes 1 and 5, one may fix the image or images formed on the surface of electrodes 1 and/or 5 by incorporating a polymeric binder material in the carrier liquid. Many such binders (which are well known for use in liquid electrophotographic liquid developers) are known to acquire a charge polarity upon being admixed in a carrier liquid and therefore will, themselves, electrophoretically migrate to the surface of one or the other of the electrodes. Alternatively, a coating of a resinous binder (which has been admixed in the carrier liquid), may be formed on the surfaces of electrodes 1 and/or 5 upon evaporation of the liquid carrier.

The electrically photosensitive colorant compounds of Formula I may be used to form monochrome images, or the compounds may be admixed with other electrically photosensitive material of proper color and photosensitivity and used to form polychrome images. Many of the electrically photosensitive compounds having Formula I have especially useful hues which make them particularly suited for use in polychrome imaging processes which employ a mixture of two or more differently colored electrically photosensitive particles. When such a mixture of multicolored electrically photosensitive particles is formed, for example, in an electrically insulating carrier liquid, this liquid mixture of particulate material exhibits a black coloration. Preferably, the specific cyan, magenta, and yellow particles selected for use in such a polychrome imaging process are chosen so that their spectral response curves do not appreciably overlap whereby color separation and subtractive multicolor image reproduction can be achieved.

The following examples illustrate the utility of the Formula I materials in electrophoretic migration imaging processes.

Examples 1–15

Imaging Apparatus

An imaging apparatus was used in each of the following examples to carry out the electrophoretic migration imaging process described herein. This apparatus was a device of the type illustrated in FIG. 1. In this apparatus, a translating film base having a conductive coating of 0.1 optical density cermet (Cr.SiO) served as electrode 1 and was in pressure contact with a 10 centimeter diameter aluminum roller 14 covered with dielectric paper coated with poly(vinyl butyral) resin which served as electrode 5. Plate 1 was supported by two 2.8 cm. diameter rubber drive rollers 10 positioned beneath film plate 1 such that a 2.5 cm. opening, symmetric with the axis of the aluminum roller 14, existed to allow exposure of electrically photosensitive particles 4 to activating radiation. The original transparency 11 to be reproduced was taped to the back side of film plate 1.

The original transparency to be reproduced consisted of adjacent strips of clear (WO), red (W29), green (W61) and blue (W47B) filters. The light source consisted of a Kodak Ektagraphic AV434A Carousel Projector with a 1000 watt Xenon Lamp. The light was modulated with a Kodak No. 5 flexible M-carbon eleven step 0.3 neutral density step tablet. The residence time in the exposure zone was 10 milliseconds. The log of the light intensity (Log I) was as follows:

| | Filters | Log I erg/cm$^2$/sec. |
|---|---|---|
| WO | Clear | 5.34 |
| W29 | Red | 4.18 |
| W61 | Green | 4.17 |
| W47B | Blue | 4.15 |

The voltage between the electrode 5 and film plate 1 was about 2 kv. Film plate 1 was negative polarity in the case where electrically photosensitive particulate material 4 carried a positive electrostatic charge, and film plate 1 was positive in the case where electrically photosensitive electrostatically charged particles were negatively charged. The translational speed of film plate 1 was about 25 cm. per second. In the following examples, image formation occurs on the surfaces of film plate 1 and electrode 5 after simultaneous application of light exposure and electric field to electrically photosensitive material evaluated for use. Electrically photosensitive particulate material 4 was admixed with a liquid carrier as described below to form a liquid imaging dispersion which was placed in nip 21 between the electrodes 1 and 5. If the material being evaluated for use as material 4 possessed a useful level of electrical photosensitivity, one obtained a negative-appearing image reproduction of original 11 on electrode 5 and a complementary image on electrode 1.

Imaging Dispersion Preparation

Imaging dispersions were prepared to evaluate each of the compounds in Table I. The dispersions were prepared by first making a stock solution of the following components. The stock solution was prepared simply by combining the components.

| | |
|---|---|
| Isopar G | 2.2 g |
| Solvesso | 1.3 g |
| Piccotex 100 | 1.4 g |
| PVT* | 0.1 g |

*Poly(vinyltoluene-co-lauryl methacrylate-co-lithium methacylate-co-methacrylic acid 56/40/3.6/0.4

A 5 g. aliquot of the stock solution was combined in a closed container with 0.045 g. of the Table I material to be tested and 12 g. of Hamber 440 stainless steel balls. The preparation was then milled for three hours on a paint shaker.

Each of the 15 materials described in Table I was tested according to the just outlined procedure. Each of such compounds was found to be electrophotosensitive as evidenced by obtaining a negative appearing image of the original on one electrode and a complementary image on the other electrode.

The invention has been described in detail with particular reference to certain preferred embodiments thereof, but it will be understood that variations and modifications can be effected within the spirit and scope of the invention.

We claim:

1. A compound having the structure:

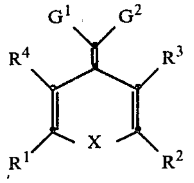

wherein

X represents O, S or NR and R is benzyl or butyl;

$G^1$ and $G^2$ represent cyano or taken together with the carbon atom to which they are attached represent sufficient atoms to complete an ethyl substituted barbituric acid nucleus;

$R^1$ and $R^2$ which may be the same or different represent $(—CH{=})_nA^1$ or $—CH{=}CH—A^2$ wherein at least one of $R^1$ and $R^2$ must be (CH) $A^1$ or $—CH{=}CH—A^2$;

$R^3$ and $R^4$ represent hydrogen or $R^3$ together with $R^2$ or $R^4$ together with $R^1$ represent sufficient atoms to form a fused substituted six-membered saturated carbocyclic ring and said carbocyclic ring substituents are selected from the group consisting of 2,3,6,7-tetrahydro-1H,5H-benzo[ij]quinolizin-9-ylmethylene and 4-(N,N-dimethylamino)benzylidene;

$A^1$ represents 3-ethylbenzoxazolin-2-ylidene or 2,6-diphenyl-4H-pyran-4-ylidene;

$A^2$ represents anthracene-9-yl; 2,3,6,7-tetrahydro-1H,5H-benzo[ij]quinolizin-9-yl; 2-styrylthiophen-5-yl; 1,2,3,4-tetrahydro-1-methylquinolin-6-yl; 4-(N,N-dimethylamino)phenyl and 4-(N-diethylamino)-2-methoxyphenyl; and n represents 1 or 3.

2. A compound according to claim 1 wherein

X represents O;

$G^1$ and $G^2$ represent cyano;

$R^1$ and $R^2$ are the same and represent —CH=• CH—$A^2$;

$A^2$ represents anthracene-9-yl; 2,3,6,7-tetrahydro-1H,5H-benzo[ij]quinolizin-9-yl or 2-styrylthien-5-yl;

$R^3$ and $R^4$ represent hydrogen.

3. A compound according to claim 1 wherein

X represents O;

$G^1$ and $G^2$ represent cyano;

$R^1$ represents —CH=$A^1$ and $A^1$ represents 2,6-diphenyl-4H-pyran-4-ylidene;

$R^2$ represents anthracene-9-yl or 2,3,6,7-tetrahydro-1H,5H-benzo[ij]quinolizin-9-yl; and $R^3$ and $R^4$ represent hydrogen.

4. A compound according to claim 1 wherein

X represents S;

$G^1$ and $G^2$ represent cyano;

$R^1$ and $R^2$ are the same and represent —CH=• CH—$A^2$;

$A^2$ represents 2,3,6,7-tetrahydro-1H,5H-benzo[ij]-quinolizin-9-yl or 1,2,3,4-tetrahydro-N-methyl-quinolin-6-yl; and $R^3$ and $R^4$ are hydrogen.

5. A compound according to claim 1 wherein

X represents NR and R is butyl or benzyl;

$G^1$ and $G^2$ represent cyano;

$R^1$ and $R^2$ are the same and represent —CH=• CH—$A^2$;

$A^2$ represents 4-(N,N-dimethylamino)phenyl, 2,3,6,7-tetrahydro-1H,5H-benzo[ij]quinolizin-9-yl or 4-(N,N-diethylamino)-2-methoxyphenyl; and $R^3$ and $R^4$ represent hydrogen.

6. A compound according to claim 1 wherein

X represents O;

$G^1$ and $G^2$ are each cyano or together with the carbon atom to which they are attached represent sufficient atoms to form an ethyl substituted barbituric acid nucleus;

$R^1$ represents phenyl;

$R^2$ represents —CH=CH—CH=$A^1$ or —CH=• CH—$A^2$;

$A^1$ represents 3-ethylbenzoxazolin-2-ylidene;

$A^2$ represents 2,3,6,7-tetrahydro-1H,5H-benzo[ij]-quinolizin-9-yl; and $R^3$ and $R^4$ represent hydrogen.

7. A compound according to claim 1 wherein

X represents O;

$G^1$ and $G^2$ represent cyano;

$R^3$ together with $R^2$ and $R^1$ together with $R^4$ represent sufficient atoms to form a fused substituted six membered saturated carbocyclic ring and said carbocyclic ring substituents are selected from the group consisting of 2,3,6,7-tetrahydro-1H,5H-benzo[ij]-quinolizin-9-ylmethylene and 4-(N,N-dimethylamino)benzylidene.

8. A compound having one of the following structure:

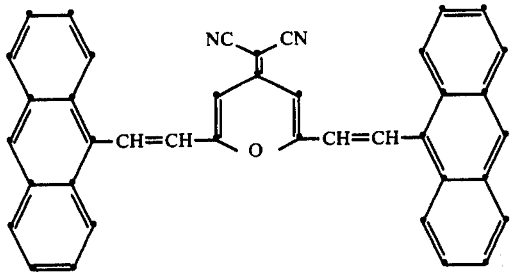

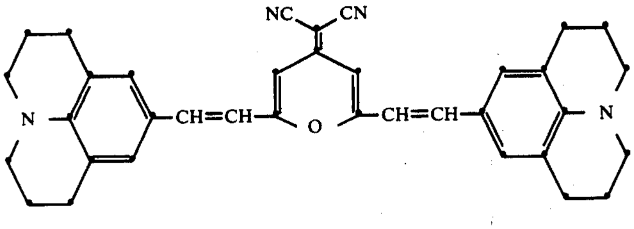

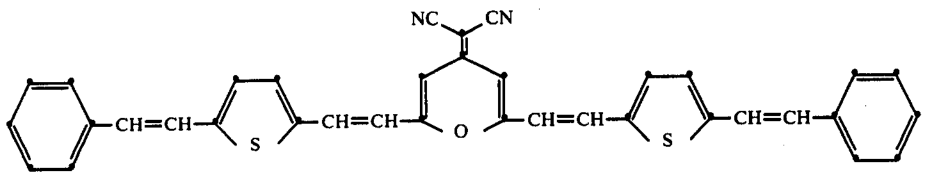

-continued
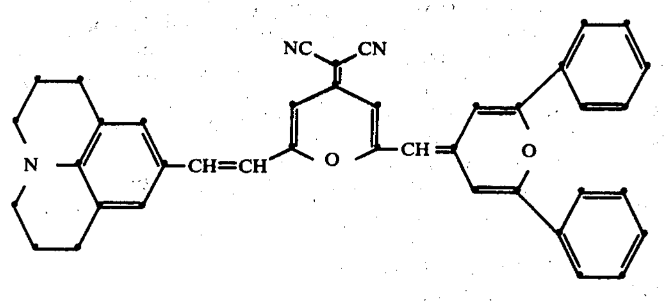
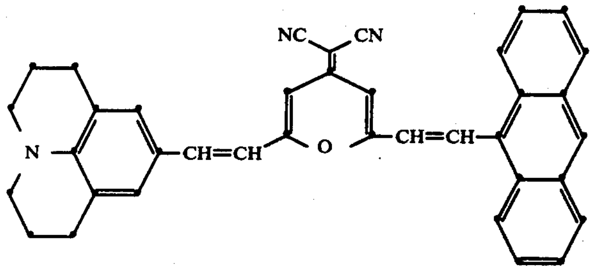
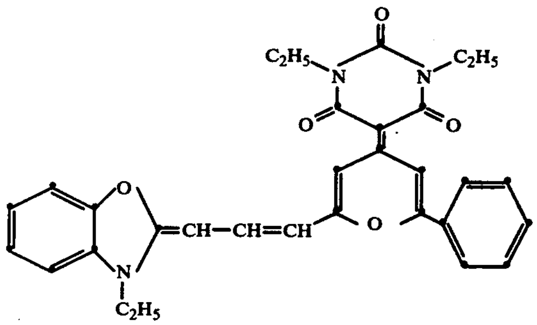
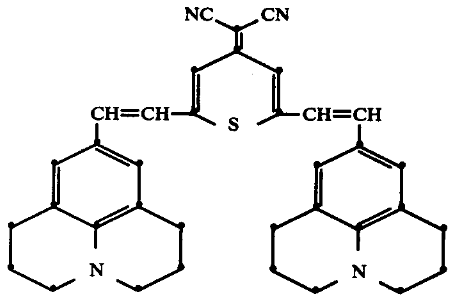
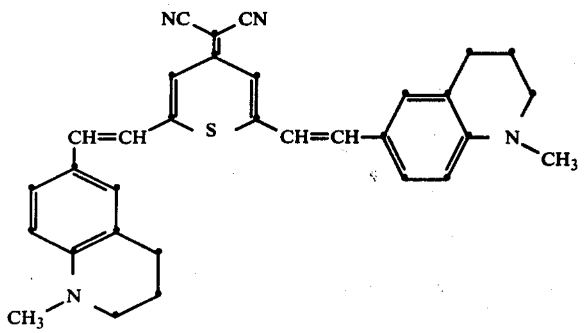

-continued
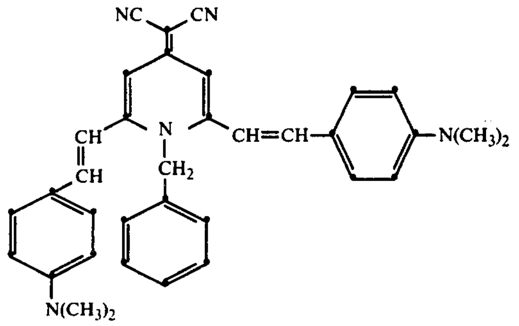
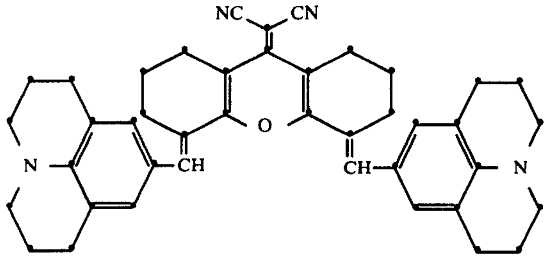
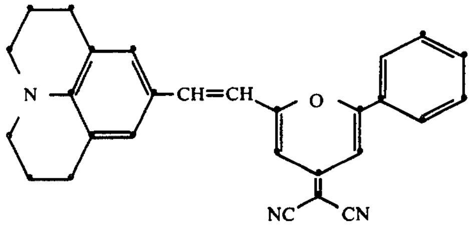
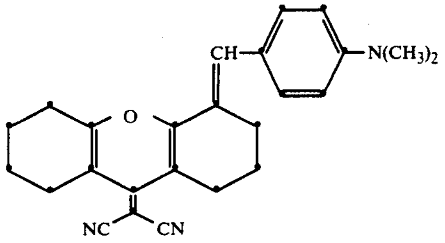
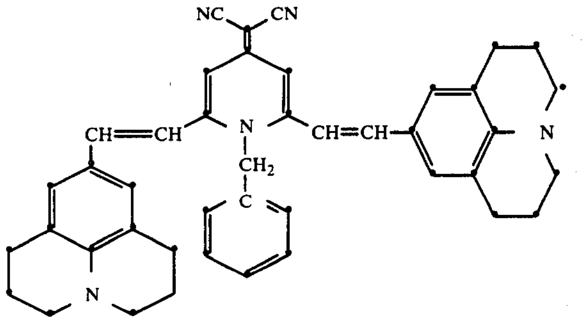
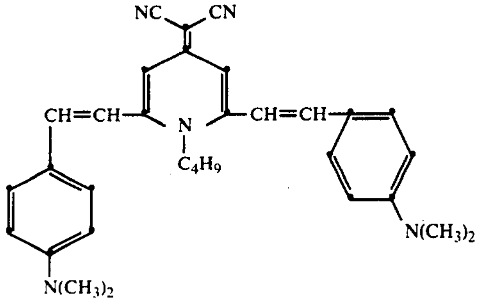
or

-continued
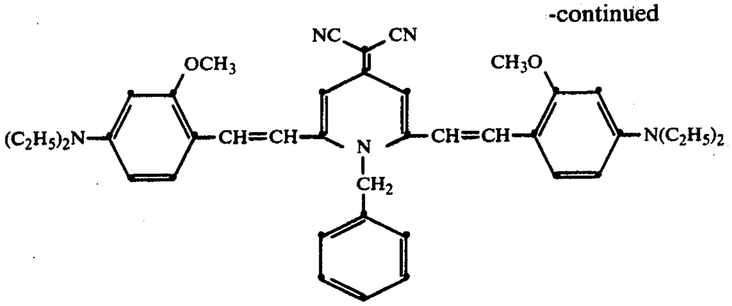
* * * * *